United States Patent
Matsuzaki et al.

(10) Patent No.: US 7,417,124 B2
(45) Date of Patent: Aug. 26, 2008

(54) ANTIBODIES SPECIFIC FOR PHOSPHORYLATION SITES AND SCREENING METHODS USING THE SAME ANTIBODIES

(75) Inventors: Koichi Matsuzaki, Hirakata (JP); Toshihito Seki, Osaka (JP); Masanori Matsushita, Kyoto (JP); Yoshiya Tahashi, Suita (JP); Fukiko Furukawa, Osaka (JP); Yasushi Sugano, Kyoto (JP); Shigeo Mori, Kobe (JP); Hideo Yamagata, Sakai (JP); Katsunori Yoshida, Moriguchi (JP); Mikio Nishizawa, Ibaraki (JP); Junichi Fujisawa, Osaka (JP); Kyoichi Inoue, deceased, late of Ashiya (JP); by Keiko Inoue, legal representative, Kobe (JP)

(73) Assignees: Zeria Pharmaceutical Co., Ltd., Tokyo (JP); Kansai Medical University, Moriguchi-Shi (JP)

( * ) Notice: Subject to any disclaimer, the term of this patent is extended or adjusted under 35 U.S.C. 154(b) by 455 days.

(21) Appl. No.: 10/822,860

(22) Filed: Apr. 13, 2004

(65) Prior Publication Data
US 2005/0079559 A1    Apr. 14, 2005

(30) Foreign Application Priority Data
Oct. 9, 2003    (JP)    ............ 2003-351259

(51) Int. Cl.
*C07K 16/00*    (2006.01)
*A61K 38/00*    (2006.01)
*A61K 38/04*    (2006.01)
*G01K 33/53*    (2006.01)

(52) U.S. Cl. .............. 530/387.1; 530/387.7; 530/387.9; 530/389.1; 530/389.2; 530/389.7; 530/300; 530/326; 530/327; 435/7.1

(58) Field of Classification Search ............... 530/387.1; 424/130.1
See application file for complete search history.

(56) References Cited

U.S. PATENT DOCUMENTS 6,103,869 A *    8/2000   Souchelnytokyi et al. ... 530/330

OTHER PUBLICATIONS

Furukawa et al. (Hepatology, Sep. 27, 2003, 38:879-889).*

Harlow and Lane (Antibodies, a Laboratory Manual, Cold Spring Harbor Laboratory Press, 1988, p. 93-94 and p. 142).*
Kretzschmar et al., "A Mechanism of Repression of TGFβ/Smad Signaling by Oncogenic Ras", Genes & Development 13:804-816 (1999), discussed in the specification.
Kretzschmar et al., Nature 389:618-622 (1997), discussed in the specification.
Heldin et al., Nature 390:465-471 (1997), discussed in the specification.
Lindemann et al; "Interfering with TGFβ-induced Smad3 nuclear accumulation differentially affects TGFβ-dependent gene expression"; Molecular Cancer 2003; 2:20; pp. 1-10.
Wang et al; "Requirement of Mitogen-activated Protein Kinase Kinase 3 . . . in Murine Mesangial Cells*"; J. Biological Chemistry; 2002; 277:49 pp. 47257-47262.
Leioven et al; "Smad3 Mediates Transforming Growth Factor-β-induced Colagenase-3 . . . Fibroblasts" J. Biological Chemistry; 2002; 277:48; pp. 46338-45346.
Bakin et al; "p38 mitogen-activated protein kinase is required for TGF-β-mediated fibroblastic transdifferentiation and cell migration;" J. Cell Science 2002; 115, pp. 3192-3206.
Tahashi et al; "Differential Regulation of TGF-β Signal in . . . Rat Liver Injury;" American Association for Liver Studies; 2002; pp. 49-61.
Matsuzaki et al; "Modulation of transforming growth factor β function in hepatocytes and hepatic stellate cells in rat liver injury;" GUT, May 2000; 46:3; pp. 719-724.
Matsuzaki et al; "Regulatory Mechanisms for Transforming Growth Factor β as an Autocrine Inhibitor . . . in its Growth;" American Association for Liver Studies 2000; pp. 218-227.
Matsuzaki et al; "Autocrine Stimulatory Mechanism by Transforming Growth Factor β in Human Hepatocellular Carcinoma"; Cancer Research 60; Mar. 1, 2000; pp. 1394-1402.
Ravanti et al; "Expression of human collagenase-3 (MMP-13) by fetal skin fibroblasts is induced by transforming growth factor-β via p38 mitogen-activated protein kinase;" FASEB J. 10-1096; published online Feb. 20, 2001.
Moustakas et al; "Smad regulation in TGF-β signal transduction"; J. Cell Science 2001; 113; pp. 4359-4369.
Date et al; "Differential expression of transforming growth factor-β and its receptors in hepatocytes and nonparenchymal cells of rat liver after CCl$_4$ administration"; J. Hepatology 1998; 28: pp. 572-581.
Heldin et al; "TGF-β signalling from cell membrane to nucleus through SMAD proteins." Nature (Dec. 1997); 390:4; pp. 465-471. (see spec. p. 2).
Kretzschmar et al; "Opposing BMP and EGF signalling pathways converge on the TGF-β family mediator Smad-1;" Nature (Oct. 1997) 389:9; pp. 618-622.

* cited by examiner

*Primary Examiner*—Karen A. Canella
*Assistant Examiner*—Peter J Reddig
(74) *Attorney, Agent, or Firm*—Kratz, Quintos & Hanson, LLP

(57) ABSTRACT

Polyclonal antibody specific for a phosphorylated linker region in Smad2 and/or Smad3.

4 Claims, 8 Drawing Sheets

(MEAN ± S.D. n=7)

DETECTION OF LOCALIZATION IN CELLS

DETECTION OF INFLUENCE BY INHIBITOR

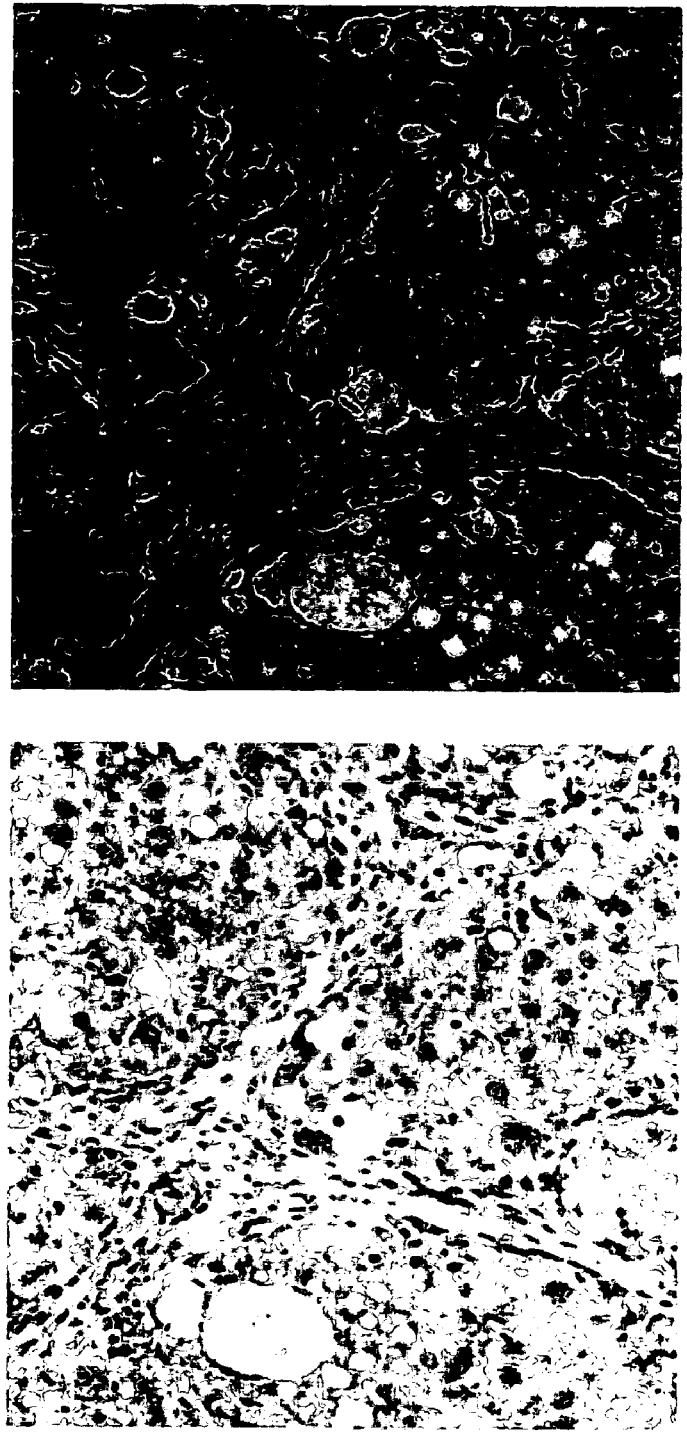

FIG. 8
α pSmad3L  α Ki-67 

ANTIBODIES SPECIFIC FOR PHOSPHORYLATION SITES AND SCREENING METHODS USING THE SAME ANTIBODIES

BACKGROUND OF THE INVENTION (1) Field of the Invention

The present invention relates to antibodies specific for phosphorylation sites and methods of screening drugs using the same antibodies. In more particular, the invention relates to novel antibodies that specifically recognize the phosphorylation site in the linker regions of Smad2 and Smad3, which are signal transduction molecules of the transforming growth factor-β (TGF-β) family. Further, the invention relates to methods of screening drugs that inhibit the phosphorylation in the linker regions of Smad2 and Smad3.

(2) Description of the Related Art

The TGF-β superfamily includes TGF-β, BMP, etc. and forms a multi-functional protein family having various physiological activities and cell regulatory functions, such as cell differentiation, growth inhibition and tissue repair, in living organisms. TGF-β is a representative cytokine of the superfamily and known to stimulate or inhibit the transcription activity of a target gene group by its signal transduction cascade.

TGF-β is known to be produced in various tissues such as platelet and act on various cells. TGF-β suppresses the growth of epithelial cells, such as hepatocyte, while promoting the accumulation of extracellular matrix (ECM) in mesenchyme cells such as fibloblast to repair tissue.

Activated Smad directly binds to the promoter region of ECM proteins, such as type I collagen and plasminogen activator inhibitor type I (PAI-1), and forms complexes with other transcription factors such as AP-I and ATF-2 to activate their transcription.

TGF-β receptors come in two types depending on the molecular weight: type I and type II and these are expressed in almost all the cells. The receptors each have serine/threonine kinase regions in the cells.

TGF-β firstly binds to its type II receptor and then to its type I receptor to form a complex. During the complex formation, the type II receptor phosphorylates the type I receptor, and then the type I receptor activated by the phosphorylation phosphorylates signal transducers called Smads which lie downstream of the TGF-β signaling system. As a result, the signals are transduced into cells (Heldin et al., Nature 390: 465-471, 1997). Smads activated by the receptor are translocated into the nucleus and act as transcription factors of target genes.

Members of the Smad protein family were identified based on the homology with Mad (mothers against Dpp) obtained by screening of genes that modified the signals of Dpp (decapentaplegic), which was a BMP homologue of Drosophila. On the other hand, genes, sma-2, -3 and -4, were obtained, which showed the same phenotype as the abnormality of gene daf-4 of receptor DAF-4, a receptor of BMP-like factor of C.elegance. Since both Sma proteins encoded by these genes, and Mad transduce the signals of the TGF-β superfamily and have a high degree of amino acid homology to one another, they are called Smad. Generally, Smad proteins are composed of about 500 amino acid residues and eight subtypes, Smad1 to Smad8, have been identified.

Smad proteins are classified into 3 types depending on their structure and function: R-Smads (receptor-regulated Smads) that are activated by type I receptor and transduce signals specific for the TGF-β and BMP signaling system, respectively; Co-Smads (common-mediator Smads) that are commonly used in all the signaling system and form complexes with R-Smads; and I-Smads (inhibitory Smads) that act in an inhibitory manner on the R-Smads and Co-Smads. As R-Smads, Smads1 to 3, 5 and 8 are known, as Co-Smads, Smad 4, and as I-Smads, Smads 6 and 7 are known.

Generally, Smads have two domains called MH1 (Mad homology 1) domain in the N-terminal region and MH2 domain in the C-terminal region, which are highly conserved among the Smad family. The MH1 domain and the MH2 domain are linked together in the region called "linker region".

It is known that in the linker regions of Smad1, Smad2 and Smad3, Ser residues are phosphorylated by Erk (Kretzschmar et al., Nature 389: 618-622, 1997; Kretzschmar et al., Genes Dev. 13: 804-816, 1999). Likewise, Ser240 and Ser260 in the linker region of Smad2 are phosphorylated by CamKII just as is Ser110 at the MH1 domain.

At the C-terminus of R-Smads there is an amino acid sequence, Ser-Ser-X-Ser (SSXS motif), and the two Sers proximate to the C-terminus are phosphrylated by TGF-β type I receptor.

Smads play a role specific for the signaling of TGF-β family members, and Smad2 and Smad3 are specific for TGF-β signaling (Heldin et al. supra). Activated Smad2 and Smad3 interact with Smad 4, which is a Co-Smad, and are translocated into the nucleus to activate target genes. TGF-β signaling activates Smad2 and Smad3 while allowing TGF-β signaling to be balanced by Smad6 and Smad7 as I-Smads.

SUMMARY OF THE INVENTION

As aforementioned, Smads are important proteins which are involved in the accumulation of TGF-β-dependent ECM proteins; therefore, the specific inhibitors of TGF-β-mediated R-Smads pathway can be clinically useful to suppress the progression of liver, kidney and lung fibrosis.

Smads are divided into three regions according to their primary structure: DNA-binding region; linker region; and regulatory region. It has been thought from the analysis using antibodies specific for the phosphorylation in the C-terminal region (Journal of Biological Chemistry 278(13): 11721-11728 (2003)) and the analysis labeling mutants that lack C-terminal region with $^{32}P$, that phophorylation in the C-terminal region plays an important role in activation of Smads by TGF-β (Journal of Biological Chemistry, supra). However, the importance of phophorylation in the linker region has been unknown without the antibodies to selectively distinguish the phosphorylation sites of R-Smads.

Smads activated with the phosphorylation have been known to be deeply involved not only in the process of fibrosis but in the process of oncogenesis. However, conventional antibodies can recognize only the phosphorylation in the C-terminal regions of Smads, so that use of such antibodies does not allow detection of the phosphorylation in their linker region. Accordingly, detecting the localization of phosphorylated Smads in a tissue using an antibody that recognizes specifically Smads phosphorylated in their linker regions can be an index of signal transduction activity via Smads in patients with systemic sclerosis or with cancer. Further, when giving such patients low-molecular compounds that inhibit the phosphorylation of Smads, if the treatment is effective, the phosphorylation in their linker regions will be reduced. And the detection of the localization of phosphorylated Smads can be means of assessing the effectiveness of molecular targeting therapy in living bodies based on objective judgment.

Under these circumstances, the present inventors directed their research effort toward the preparation of antibodies capable of distinguishing the phosphorylation in the linker region of Smad2 and Smad3 and performed analysis of phosphorylation in the linker region using the antibodies; consequently, they have found that not only phosphorylation in the C-terminal region, but also phosphorylation in the linker region play a very important part in the activation of Smads. Particularly the analysis confirmed that Smad3 phosphorylated in the linker region existed in nuclei indicating that the activated Smad3 might constitutively stimulate the production of ECM proteins under pathological conditions.

Thus, it is possible to suppress the transcription of ECM proteins specifically under the pathological conditions where ECM proteins are continuously produced, by inhibiting phosphorylation in the linker region, which does not cause a substantially detrimental influence under the physiological conditions.

The present inventors' immunohistochemical study using the antibodies of this invention confirmed that Smads phosphorylated in their linker regions were detected in rat hepatic fibrosis tissues as well as in human colon cancer tissues and that the phosphorylation of Smads was increased with the aggravation of the symptoms.

Thus examining the localization of phosphorylated Smads in such tissue using the antibodies of this invention can be an index of signal transaction activity in cancer and systemic sclerosis and means of assessing the effectiveness of the molecular targeting therapy.

The present invention relates to polyclonal antibody specific for a phosphorylated linker region in Smad2 and/or Smad3.

Also, the invention relates to polyclonal antibody that binds specifically to phosphorylated Smad2 and/or phosphorylated Smad3. The antibody was obtained from the antisera raised by immunizing a mammal such as rabbit with a phosphorylated product of a peptide including an amino acid sequence of the linker region in Smad2 and/or Smad3.

Further, the invention relates to a method of screening drugs that inhibit phosphorylation of the linker region in Smad2 or Smad3, including the steps of:
(i) bringing mammalian cells, in which TGF-β receptor is intrinsically expressed or overexpressed, into contact with a candidate drug before treating the cells with TGF-β;
(ii) incubating the above cells together with TGF-β;
(iii) recovering and homogenizing the cells after the incubation to obtain a homogenate;
(iv) incubating the obtained homogenate together with an antibody(ies) specific for a Smad protein(s) to form immunoprecipitate; and
(v) detecting the presence or absence of a phosphorylated Smad protein(s) by reacting the immunoprecipitate with the polyclonal antibody of the invention to evaluate the inhibition of phosphorylation.

Still further, the invention relates to a method of screening drugs that inhibit phosphorylation of a Smad protein(s), including the steps of:
(i) bringing a Smad protein(s), as a substrate(s), into contact with a candidate drug;
(ii) reacting the above Smad protein(s) with active p38 in the presence of ATP; and
(iii) detecting phosphorylated Smad protein(s) in the reacted Smad protein(s) to infer the inhibition of phosphorylation.

Still yet further, the invention relates to a method of screening drugs that inhibit phosphorylation of a Smad protein(s), including the steps of:
(i) stimulating arbitrary cells with TGF-β and recovering the cells after a predetermined time;
(ii) immunoprecipitating a homogenate of the recovered cells with an antibody(ies) specific for a kinase;
(iii) incubating the above immunoprecipitated samples, a candidate drug(s), recombinant Smad2 and recombinant Smad3 and phosphorylating Smad2 and Smad3 in vitro; and
(iv) detecting a phosphorylated Smad protein(s) in the reacted Smad proteins by immunoblotting technique using an antibody(ies) against phosphorylation in the linker region to evaluate the inhibition of phosphorylation.

Still yet further, the invention relates to a method of immunohistochemically detecting phosphorylated Smads using the above antibodies. Specifically, the invention relates to a method of assessing an index of pathological signal transduction activity and the effectiveness of the molecular targeting therapy in systemic sclerosis and cancer, including the step of incubating the antibody of this invention with a sample of the object tissue.

According to the antibody and the screening method of this invention, not only Smad phosphorylation inhibitors, but also anti-fibrosis drugs can be screened more efficiently and specifically than conventional methods in which phosphorylation in the C-terminal region alone is detected without discriminating between the phosphorylation in the linker region and that in the C-terminal region.

Further, use of the antibody of this invention enables not only the assessment of the pathological signal transduction activity in systemic sclerosis and cancer tissues, but also objective judgment of efficacy of drugs used for such patients.

BRIEF DESCRIPTION OF THE DRAWINGS

FIG. 6 illustrates the result of immunohistochemical examination using tissue sections that shows linker region-phosphorylated Smad3 is detected specifically in nuclei of collagen producing cells with the progress of disease.

FIG. 8 illustrates the detection of the phosphorylation in the linker region of Smad3 in human colon cancer tissues by the antibodies of this invention.

PREFERRED EMBODIMENT OF THE INVENTION

The present invention relates to polyclonal antibodies specific for phosphorylated linker regions in Smad2 and Smad3.

The polyclonal antibodies in accordance with this invention can be obtained from antisera raised by immunizing mammals with the phosphorylated products of peptides including the amino acid sequences of the linker regions in Smad2 and Smad3.

The immunized mammal is preferably a rabbit, a goat, a mouse or the like.

The polyclonal antibodies in accordance with this invention are specific for the phosphorylated linker regions in Smad2 and Smad3.

Figure 1:
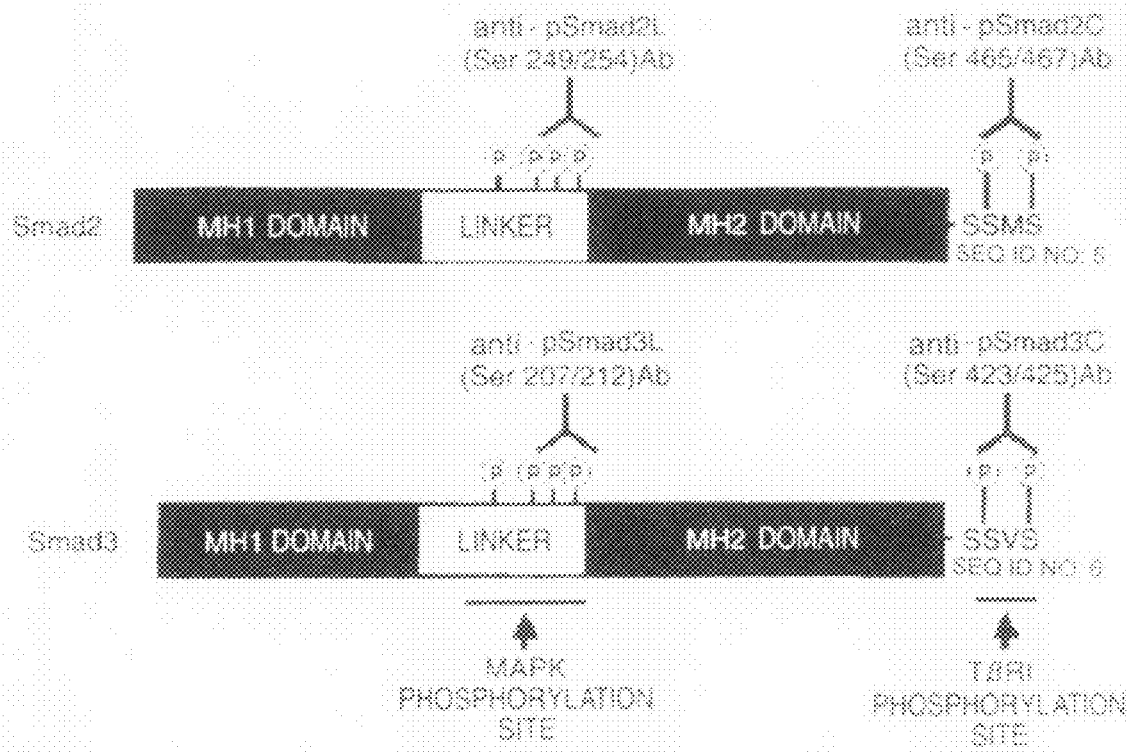
FIG. 1 illustrates the positions of the peptides used on the primary structures of Smad2 and Smad3.
Figure 2A:
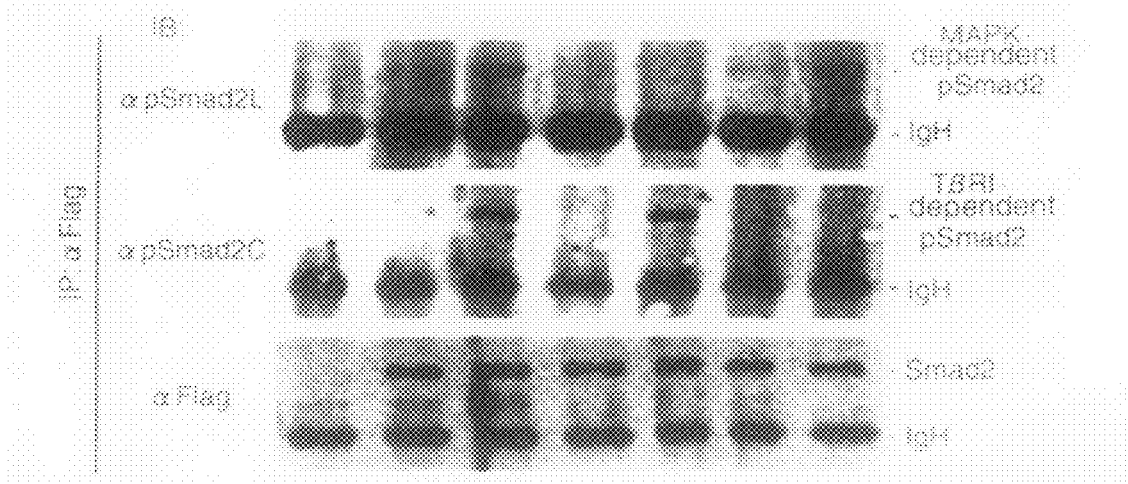
FIG. 2A illustrates the specificity of Smad2 antibodies ascertained using clone 9 cells.
Figure 2B:
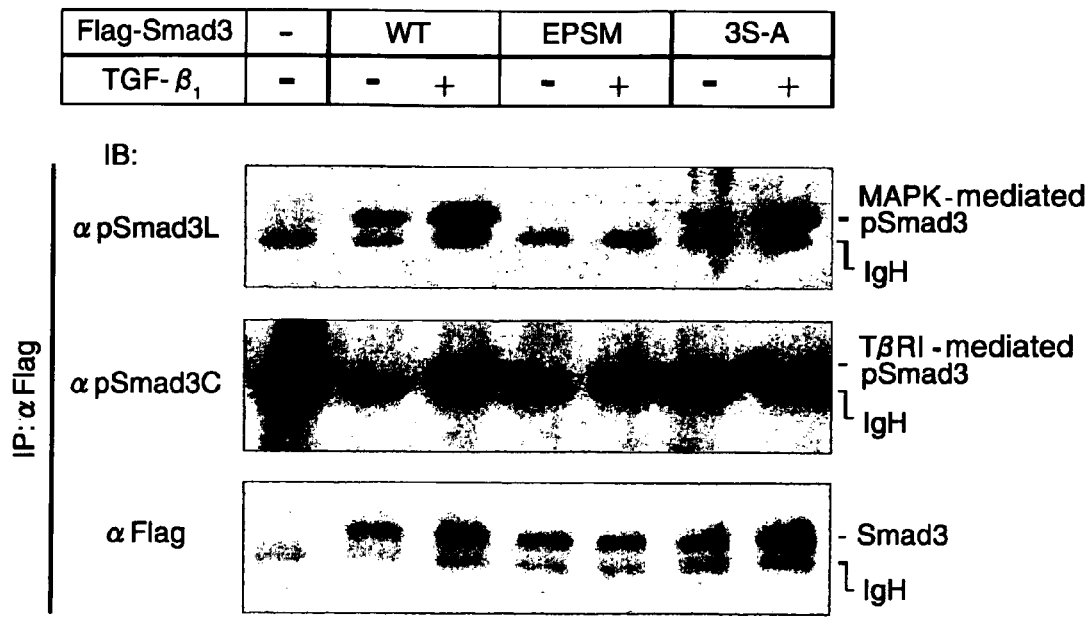
FIG. 2B illustrates the specificity of Smad3 antibodies ascertained using clone 9 cells.
Figure 2C:
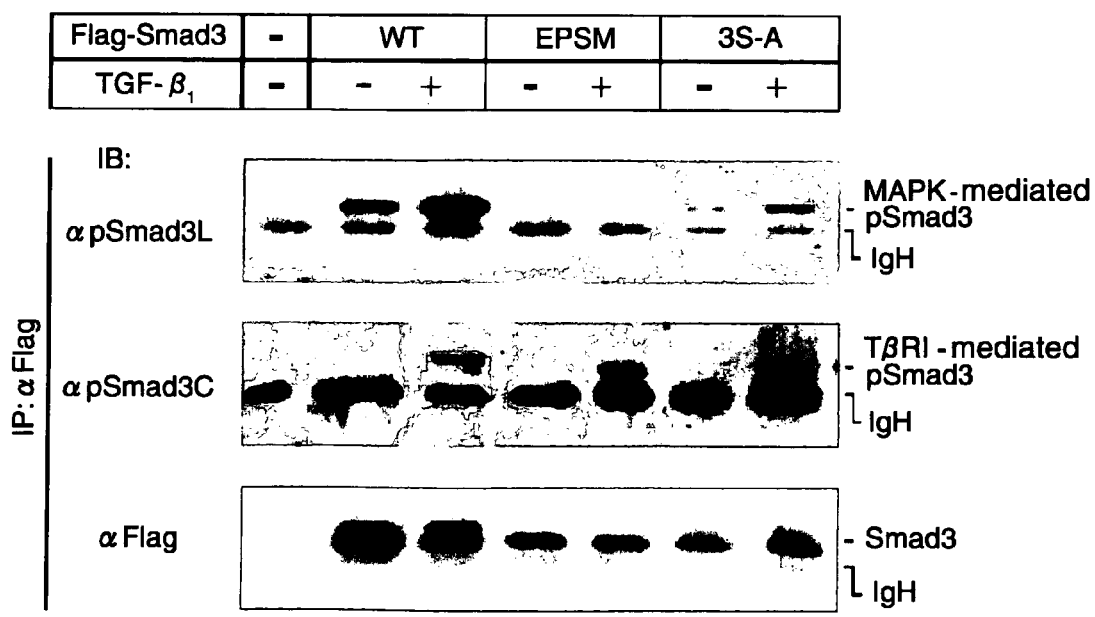
FIG. 2C illustrates the specificity of Smad3 antibodies ascertained using MFB cells.

The amino acid sequences of Smad2 and Smad3 including the linker regions and the C-terminal regions are shown in Genbank: NM_005901 (human Smad2) and Genbank: NM_005902 (human Smad3), respectively. The positions of peptides phosphorylated are schematically shown in FIG. 1. FIG. 1 shows functional domains of Smad proteins in terms of their primary structure. Smad proteins each have the MH1 domain in the N-terminal region and the MH2 domain in the C-terminal region, and the region that links the two domains is called linker region. Both Smad2 and Smad3 proteins possess major phosphorylation sites: four sites in their linker regions and two sites in the C-terminal regions.

Specifically, the positions are as follows.

Phosphorylated peptide in the linker region of Smad2 corresponds to its amino acid residues at positions 245 to 259 and is represented by:

Pro Ala Glu Leu p-Ser Pro Thr Thr Leu p-Ser Pro Val Asn His Ser (SEQ ID NO: 1)

wherein p-Ser represents phosphorylated serine and the positions of p-Ser correspond to 249 and 254.

Phosphorylated peptide in the linker region of Smad3 corresponds to its amino acid residues at positions 201 to 214 and is represented by:

Ala Gly Ser Pro Asn Leu p-Ser Pro Asn Pro Met p-Ser Pro Ala (SEQ ID NO: 2)

wherein p-Ser represents phosphorylated serine and the positions of p-Ser correspond to positions 207 and 212.

Phosphorylated peptide in the C-terminal region of Smad2 corresponds to its amino acid residues at positions 459 to 467 and is represented by:

Pro Ser Val Arg Cys Ser p-Ser Met p-Ser (SEQ ID NO: 3)

wherein p-Ser represents phosphorylated serine and the positions of p-Ser correspond to positions 465 and 467.

Phosphorylated peptide in the C-terminal region of Smad3 corresponds to its amino acid residues at positions 417 to 425 and is represented by:

Pro Ser Ile Arg Cys Ser p-Ser Val p-Ser (SEQ ID NO: 4)

wherein p-Ser represents phosphorylated serine and the positions of p-Ser correspond to positions 423 and 425.

The polyclonal antibodies in accordance with this invention are preferably obtained by affinity purification with phosphorylated peptides. For example, affinity columns (activated Thiol Sepharose 4B, Amersham Biosciences etc.) of phosphorylated peptides in the linker regions and in the C-terminal regions of Smad2 and Smad3 are prepared and the antibodies are affinity purified.

In the following, a method will be described of forming antibodies specific for the phosphorylated peptides in the linker regions of Smad proteins.

Antisera are obtained by immunizing mammals, such as a rabbit, with the above described 4 types of phosphorylated peptides specific for the linker regions of Smad2 and Smad3 and the C-terminal regions of Smad2 and Smad3. Antisera are affinity purified with phosphorylated peptides to obtain specific polyclonal antibodies.

The polyclonal antibodies specific for the linker regions of phosphorylated Smad2 and of phosphorylated Smad3 can be used in a method of screening drugs that inhibit phosphorylation of the linker regions of Smad2 and Smad3.

Thus, the method in accordance with this invention of screening drugs (also referred to as candidate drug in this specification), which are to be examined whether or not they inhibit phosphorylation in the linker regions of Smad2 and Smad3, includes at least the steps of:

(i) bringing mammalian cells, in which TGF-β receptor is expressed natively or overexpressed, into contact with candidate drugs before treating the cells with TGF-β;

(ii) incubating the above cells together with TGF-β;

(iii) recovering and homogenizing the above cells after the incubation (iv) incubating the obtained homogenate together with an antibody(ies) specific for a Smad protein(s) to form an immunoprecipitate; and (v) detecting the presence or absence of a phosphorylated Smad protein(s) by reacting the above immunoprecipitate with the polyclonal antibody according to this invention to evaluate the inhibition of phosphorylation.

In the steps (i) to (v) described above are used mammalian cultured cells in which TGF-β receptor is intrinsically expressed or overexpressed, or cells in which fusion proteins of Smad2 or Smad3 tagged with GST, FLAG, etc. depending on the situation have been expressed. The cells are stimulated by TGF-β, recovered after an arbitrary time, and homogenized. The cell homogenate is immunoprecipitated with a known Smad-specific antibody. Known Smad-specific antibodies include, for example, anti-Smad2/Smad3 antibodies available from Santa Cruz Biotechnology, Upstate Biotechnology, or Signal Transduction Lab. Then, the region-specific phosphorylation kinetics is confirmed with antibodies that recognize specifically Smad2 and Smad3 phosphorylated in the linker regions (hereinafter also referred to as Smad2 and Smad3 phosphorylation-specific antibodies). In this sequence of steps, whether or not a candidate drug inhibits phosphorylation of Smad2 and Smad3 can be evaluated by treating the cells with the candidate drug, incubating the same with TGF-β and further incubating same with antibodies specific for Smad proteins to form immunoprecipitates, and reacting the formed complexes with the polyclonal antibodies of this invention which are specific for the phosphorylated linker regions of Smad2 and Smad3, to detect the presence or absence of phosphrylated Smad proteins. In other words, if the polyclonal antibodies detect phosphorylated Smad proteins in the cells, it is considered that the linker regions of Smad2 and Smad3 in the cells have been phosphrylated by the TGF-β signaling and the candidate drug is not a drug that inhibits phosphorylation of Smads. On the other hand, if the polyclonal antibodies do not detect phosphorylated Smad proteins in the cells, it is considered that the linker regions have not been phosphrylated by the TGF-β signaling and the candidate drug is a drug that inhibits phosphorylation of Smads. Thus, compounds that inhibit specifically phosphorylation of Smads by TGF-β can be screened depending on the objective.

The screening method described above can be incorporated to discover drugs, as one step of the process, that inhibit phosphorylation in the linker regions of Smad2 and Smad3.

Those skilled in the art will readily recognize from the disclosure in this specification that the above described screening method constitutes one part of the above drug discovery process.

The drugs thus obtained inhibit phosphorylation in the linker regions of Smad proteins and are useful as anti-fibrosis drugs against, for example, continuous production of collagen, which is one of the nonphysiological actions of TGF-β.

As another aspect of the screening method of this invention, a method of screening drugs that inhibit phosphorylation of Smad proteins, in which p38 is used, includes at least the steps of:
  (i) bringing a Smad protein(s) as a substrate(s) into contact with candidate drugs;
  (ii) reacting the above described Smad protein(s) with active p38 in the presence of ATP; and
  (iii) detecting phosphorylated Smad protein(s) in the reacted Smad protein(s) to evaluate the inhibition of phosphorylation.

This screening method uses the so-called in vitro kinase assay. In in vitro kinase assay, a kinase is reacted with a substrate (in this invention, a Smad protein) in a test tube in the presence of ATP to phosphorylate the substrate. In other words, the assay makes it possible to ascertain whether Smad proteins are directly phosphorylated or not, not by intracellular reaction and under conditions free of any intervening substances.

As still another aspect of the screening method of this invention, a method of screening drugs that inhibits phosphorylation of Smad proteins using recombinant Smads includes at least the steps of:
  (i) stimulating arbitrary cells with TGF-β and recovering the cells after a predetermined time;
  (ii) immunoprecipitating the homogenate of the recovered cells with a specific antibody(ies) for a kinase;
  (iii) incubating the immunoprecipitated sample, a candidate drug(s), recombinant Smad2 and recombinant Smad3 and phosphorylating Smad2 and Smad3 in vitro; and
  (iv) detecting a phosphorylated Smad protein(s) in the reacted Smad proteins by an immunoblotting technique using an antibody(ies) against phosphorylation in the linker region to evaluate the inhibition of phosphorylation.

Specifically, kinases are prepared in such a manner as to cultivate cells under serum-free conditions, treat the cells with TGF-β, recover the treated cells after a certain time, immunoprecipitate phosphorylated JNK or phosphorylated p38 which is active kinase (these enzymes become active when they are phosphorylated) with their specific antibodies (available from Promega), isolate the phosphorylated JNK or phosphorylated p38-antibody complex with protein G-Sepharose, and wash and suspend the immunoprecipitated enzymes in a kinase buffer. Two micrograms of bacterial recombinant GST-Smad3 and GST-Smad2 are reacted with the kinases in 50 μl of kinase buffer containing 100 μM ATP. Separation by SDS-polyacrylamide gel electrophoresis is performed, and phosphorylated Smads are detected by quantifying the consumed ATP using chemiluminescence or by an immunoblotting technique using the antibodies specific for phosphorylation.

The term "specific antibody against kinase" herein used means a specific antibody against an active enzyme, such as p38 or JNK (c-Jun N-terminal kinase). Both p38 and JNK are activated when they are phosphorylated, and antibodies against the above active enzymes include:

Anti-Active p38 Antibody (Anti-Active p38/pTGpY, Rabbit. Manufacturer: Promega)
  antibody specific for the p38 in which Thr at position 182 and Tyr at position 184 are phosphorylated among its phosphorylation sites: Thr at position 182; Gly at position 183; and Tyr at position 184. and Anti-Active JNK Antybody (Anti-Active JNK/pTPpY, Rabbit. Manufacturer: Promega)
  antibody specific for JNK in which Thr at position 183 and Tyr at position 185 are phosphorylated among its phosphorylation sites: Thr at position 183; Pro at position 184; and Tyr at position 185.

The terms "Smad2 recombinant" and "Smad3 recombinant" herein used mean recombinant proteins obtained by fusing the N-terminals of Smad3 and Smad2 with GST. The recombinant Smad2 and the recombinant Smad3 in this invention are produced using $E.\ coli$ (DH5α). Plasmids containing GST-Smad2 and GST-Smad3, which are constructed so as to be inducibly expressed by IPTG (isopropyl-thio-β-D-galactopyranoside), are integrated into $E.\ coli$ cells. And the cells are cultured overnight, the GST-Smad2 and GST-Smad3 are expressed by IPTG, and the cells are disrupted by sonication. The centrifugation supernatant of the obtained extract is applied onto a Glutathione Sepharose 4B column and washed with PBS (−) and 50 mM Tris-HCl buffer, pH 8.0, and the GST-Smad proteins are eluted with 50 mM Tris-HCl buffer, pH 8.0, containing 10 mM reduced glutathione. The GST-Smad3 and the GST-Smad2 thus obtained are used for tests.

The use of the antibodies in accordance with this invention has confirmed that the linker region of Smad3 is phosphorylated by p38 and JNK. If this reaction system is treated with candidate compounds, compounds that inhibit phosphorylation can be screened.

The present inventors' immunohistochemical study of phosphorylation dynamics of Smads in a human colon cancer tissue using the antibodies of this invention revealed that Smad3 phosphorylated in its linker region was specifically detected in the cancer tissue. Also, it revealed that the phosphorylation of Smad3 in its linker region was increased with the aggravation of the cancer, indicating positive correlation between the phosphorylation of Smad3 in its linker region and the degree of malignancy of the cancer.

(1) Liver Fibrosis Signal Transduction Mechanism via Smads

The present inventors prepared 4 types of antibodies against phosphorylated Smad2 and Smad3. They were specific for the linker regions of Smad2 and Smad3 phosphorylated by MAP kinase (MAPK), and for their C-terminal regions phosphorylated by type I TGF-β receptor. Further, after the examination using cultured myofibroblasts, the inventors found that Smad3 phosphorylated by active p38 MAPK stimulated the production of extracellular matrix (ECM). The inventors compared and examined the phosphorylation levels of Smad2 and Smad3 in activated hepatic stellate cells (HSCs) and myofibroblast (MFB) of injured liver tissue using the antibodies and made clear the signal transduction mechanism via Smads.

Three to five rabbits were immunized with phosphorylated peptides specific for the respective sites so as to obtain antisera. Of the obtained antisera, only antisera specific for the phosphorylated Smads were selected and affinity purified with immunized peptides so as to enhance their antigen specificity.

In rats with acute liver injury, loss of hepatocytes and severe inflammatory cell infiltration were observed around their central venous region 36 hours after CCl₄ administration and improved 72 hours after the administration.

α Smooth Muscle Actin- and Vimentin-positive HSCs were observed in their central venous region of the liver injury by immunohistochemical examination. In activated HSCs of the injured liver, Smad3 phosphorylated in the linker region and Smad2 and Smad3 phosphorylated in C-terminal region were observed in the nucleus, whereas they were not observed in normal liver. Smad2 phosphorylated in the linker region was observed in the cytoplasm.

Stellate cells were isolated from rat liver and immunoprecipitated with anti-Smad2 and anti-Smad3 antibodies, and their phosphorylated state was analyzed by western blotting. In normal stellate cells, almost no Smad2 and Smad3 were phosphorylated. Phosphorylation increased and reached its peak 36 hours after the administration at all of the linker regions and the C-terminal regions of Smad2 and Smad3 and was decreased 72 hours.

It was observed by histological examination of rats with chronic liver injury that their lobular structure was reconstructed, 3 to 6 weeks after the continuous CCl₄ administration, with the progress of fibrosis.

It was also observed by immunohistological examination that MFB-like cells along the fibrous bundle in the injured liver were a SMA and Vimentin positive. In the MFB-like cells, Smad3 phosphorylated in the linker region and Smad2 phosphorylated in C-terminal region were observed in the nuclei and Smad2 phosphorylated in the linker region was observed in the cytoplasm. However, Smad3 phosphorylated in C-terminal region was not observed.

The MFB-like cells were isolated and their phosphorylated state was analyzed by western blotting. Intensive phosphorylation was observed in the linker regions of Smad2 and Smad3 and the C-terminal region of Smad2 within 6 weeks after the continuous administration with CCl₄. However, phosphorylation was not observed in the C-terminal region of Smad3 regardless of increased TGF-β in blood.

This may be because unlike HSC cells after acute liver injury, in MFB cells during chronic liver injury, the linker region of Smad3 is constantly phosphorylated with the activation of p38 MAPK and translocated into nucleus, as a result, the C-terminal cannot be phosphorylated by type I TGF-β receptor.

(2) Analysis of TGF-β Signal Transduction Mechanism Using Antibodies Specific for Phosphorylated Smad2 and Smad3 in Primary Cultured Stellate Cells The present inventors already reported the significance of TGF-β signal transduction in liver disease (Hepatology 2002, 35: 49-61).

The inventors further focused their study on phosphorylation of Smad2 and Smad3 by TGF-β and have made clear the difference between the signal transduction via Smad2 and that via Smad3 in primary cultured HSCs, using antibodies specific for phosphrylated Smad2 and phosphrylated Smad3.

Three to five rabbits were immunized with phosphorylated peptides specific for the respective sites. Of the obtained antisera, only antisera specific for the phosphorylated Smads were selected and affinity purified with immunized peptides so as to enhance their antigen specificity.

The primary cultured HSCs were isolated and cultured by conventional procedure, and TGF-β was added to the cultured cells. Five minutes after the addition of TGF-β, not only the C-terminal regions of Smad2 and Smad3, but the linker region of Smad3 was markedly phosphorylated almost simultaneously. TGF-β treatment caused a minimal increase in Smad2 phosphorylation in the linker region.

Smad3 phosphorylation in the linker region was increased, accompanied by activation of p38 MARK, when TGF-β was added, but decreased when the inhibitor was added.

The phosphorylation in the linker region of Smad2 stimulated dimer formation with Smad4. However, to translocate Smad2 into nucleus, C-terminal phosphorylation is required for the nuclear translocation of Smad2.

After the addition of TGF-β, in Smad3, the C-terminal region was phosphorylated by type I receptor, even when the linker region was not phosphorylated, and it formed a dimer with Smad4 and was translocated into nucleus. The Smad3-Smad4 complex existed at the Smad-binding site on the promoter region in Smad7 gene, and stimulated the transcriptional activity.

Conversely, even when the C-terminal region was not phosphorylated, the linker region was phosphorylated by the stimulation by p38 MAPK, and Smad3 formed a dimer with Smad4 and was translocated into nucleus. The Smad3-Smad4 complex also existed at the Smad-binding site on Smad7 promoter, however, surprisingly it did not stimulate the transcriptional activity of Smad7.

It is considered that the p38 MAPK-dependently phosphorylated Smad3 transduced signal independently of the type I TGF-β-dependently phosphorylated Smad3. The present inventors considered that to activate the Smad7 transcription in primary cultured HSCs, phosphorylation at the C-terminal of Smad3 was necessary.

(3) Analysis of TGF-β Signal Transduction Mechanism Using Antibodies Specific for Phosphorylated Smad2 and Smad3 in Cultured Myofibroblasts Myofibroblasts transformed with the activation of HSCs are known to play an important role in stimulating liver fibrosis. TGF-β is a key cytokine that develops liver fibrosis. However, there has been no report on the analysis of TGF-β signal transduction that uses, as an index, site-specific phosphorylation of Smad2 and Smad3, which are TGF-β signal transduces in cultured myofibroblasts.

The present inventors focused their study on phosphorylation of Smad2 and Smad3 and have made clear, using the phosphorylation antibodies, the signal transduction mechanism via Smads in cultured myofibroblasts.

Three to five rabbits were immunized with phosphorylated peptides specific for the linker regions and the C-terminal regions of Smad2 and Smad3.

The primary cultured HSCs were isolated and cultured by conventional procedure, and the activated HSCs on 14th day (myofibroblast-like cells) were used in experiments. The phosphorylation of Smad2 and Smad3 was examined by western blotting using antibodies against Smad2 and Smad3 which were site-specifically phosphorylated after the immunoprecipitation with anti-Smad2 antibody and anti-Smad3 antibody. In the cells used, the linker regions of Smad2 and Smad3 and the C-terminal region of Smad2 had been already phosphorylated. The addition of TGF-β caused marked phosphorylation not only in the C-terminal region of Smad2, but also in the linker region of Smad3. However, the C-terminal region of Smad3 was not phosphorylated.

p38 MAPK was also phosphorylated in proportion to the phosphorylation in the linker region of Smad3 and was markedly phosphrylated when adding TGF-β. From the fact that phosphorylation in the linker region of Smad3 was decreased by a p38 MAPK inhibitor, the present inventors consider that TGF-β-activated p38 MAPK is involved in phosphorylation.

Smad3 phosphorylated by p38 MAPK formed a dimer with Smad4 and was translocated into nucleus. The Smad3-Smad4 complex existed at the Smad-binding site on the promoter region in plasminogen activator inhibitor (PAI-1) gene, which was one of ECM proteins, and promoted the transcriptional activity thereof.

The present inventors surmise that unlike primary cultured HSCs, in myofibroblast, p38 MAPK is activated, and the linker region of Smad3 was constantly phosphorylated and translocated into nucleus, as a result, the C-terminal cannot be phosphorylated by type I TGF-β receptor. The inventors also consider that the Smad3 phosphorylated in the linker region is highly involved in continuous accumulation of ECM proteins in the cells.

EXAMPLE 1

Preparation of Antibodies Specific for Linker Region-Phosphorylated Smads and Ascertainment of Specificity (1) Outline of Results Phosphorylated peptides specific for the linker regions and the C-terminal regions in Smad2 and Smad3:
Pro Ala Glu Leu p-Ser Pro Thr Thr Leu p-Ser Pro Val Asn His Ser (SEQ ID NO: 1)
Ala Gly Ser Pro Asn Leu p-Ser Pro Asn Pro Met p-Ser Pro Ala (SEQ ID NO: 2)
Pro Ser Val Arg Cys Ser p-Ser Met p-Ser (SEQ ID NO: 3)
Pro Ser Ile Arg Cys Ser p-Ser Val p-Ser (SEQ ID NO: 4)

wherein p-Ser represents phosphorylated serine were prepared, each of the peptides was conjugated with bovine thyroglobulin used as carrier protein, and the mixture of each of the conjugates and an adjuvant was prepared. Three to five rabbits were immunized with the mixture, and then booster was given 4 to 7 times every 2 weeks in the same manner as above. Finally, blood samples were collected from the rabbits to obtain antisera. Then, affinity columns (Activated Thiol Sepharose 4B, Amersham Biosciences) of linker region and C-terminal region peptides of phosphorylated Smad2 and Smad3 were prepared and used to affinity purify each antibody. Specifically, the antisera obtained were applied onto the affinity columns of phosphorylated peptides and the antibodies were eluted with 0.2 M glycine-HCl buffer (pH 2.5), and fractions containing specific antibodies were collected to give purified antibodies. The positions of the peptides used on the primary structures of Smad proteins are shown in FIG. 1.

(2) Method

Smad2 and Smad3 phosphorylated in the linker regions were detected and the specificity of the antibodies was ascertained.

Cultured cells in which TGF-β receptors were intirinsically expressed or overexpressed, or cells in which Flag-Smad2 or Smad3 had been expressed were stimulated with TGF-β, recovered after an arbitrary time, and homogenized. After the cell homogenates were immunoprecipitated with Flag antibodies, the region-specific phosphorylation kinetics was ascertained with antibodies specific for the phosphorylated Smad2 and Smad3. The concrete operations were as follows.

FLAG-tagged Smad3cDNA and FLAG-tagged Smad2cDNA (WTs), cDNAs (EPSM) lacking of the phosphorylation sites in the linker region of the above WTs, and cDNAs (3S-A) lacking of the phosphorylation sites in the C-terminal region of the above WTs were prepared and expression vectors that allow constitutive expression in the presence of CMV promoters were constructed. As cells were used those obtained by culturing hepatic stellate cells (HSCs) isolated from CCl$_4$-treated rats and purified, as described above, and differentiating the same into myofibroblast-like cells, and hepatic cells, clone 9 (I. B., Weinstein et al., Cancer Res. 35, 253-263 (1975)), established from rat normal liver. Specifically, vectors were introduced into myofibroblast (2×10$^6$ cells/100 mm dish) from rat liver cultured in DMEM medium (containing 5% fetal bovine serum) and into clone 9 cultured under the serum-free conditions, respectively, by lipofection technique using lipofectAMINE (invitrogen). After washed, the cells were cultured for 36 hours and cultured with 200 pM TGF-β (R&D Systems) for 30 minutes under the serum-free conditions. The cells were homogenized with RIPA buffer (10 mM Tris-HCl, pH 7.8/1% NP40/0.15M NaCl/1 mM EDTA/10 μg/ml aprotinin), and the resultant lysate was centrifuged at 15,000×g. The supernatant was incubated with anti-FLAG antibody (sigma) and protein G-sepharose (Amersham Bioscience) to obtain immunoprecipitate. After the incubation, part of the precipitate was subjected to SDS-polyacrylamide gel electrophoresis, the obtained gel was transferred onto a PVDF membrane, and immunoblotting was performed using the antibodies specific for phosphorylation of the linker regions and C-terminal regions in Smad2 and Smad3. The detection was carried out by chemiluminescence technique using HRP-labeled secondary antibody/anti-IgG, IgH antibody (Amersham Bioscience). The detection showed that the antibodies against phosphorylation in the linker regions did not recognize the proteins (EPSM) lacking of the phosphorylation sites in the linker region and the antibodies against phosphorylation in the C-terminal regions did not recognize the proteins (3S-A) lacking of the phosphorylation sites in the C-terminal regions. Thus the specificity of each antibody was ascertained.

3S-A was a mutant in which two C-terminal phosphorylation sites, Ser (serine) residues, were changed to Ala (alanine). The positions of phosphorylation sites of Smad2 and Smad3 were positions 423 and 425 for Smad3 and positions 465 and 467 for Smad2.

EPSM was a mutant in which three linker phosphorylation sites, Ser residues, were changed to Ala and one Thr residue to Val. The positions of phosphorylation sites of Smad2 and Smad3 were Thr residue at position 178 and Ser residues at positions 203, 207 and 212 for Smad3 and Thr residue at position 220 and Ser residues at positions 245, 250 and 255 for Smad2.

EXAMPLE 2

Figure 3:
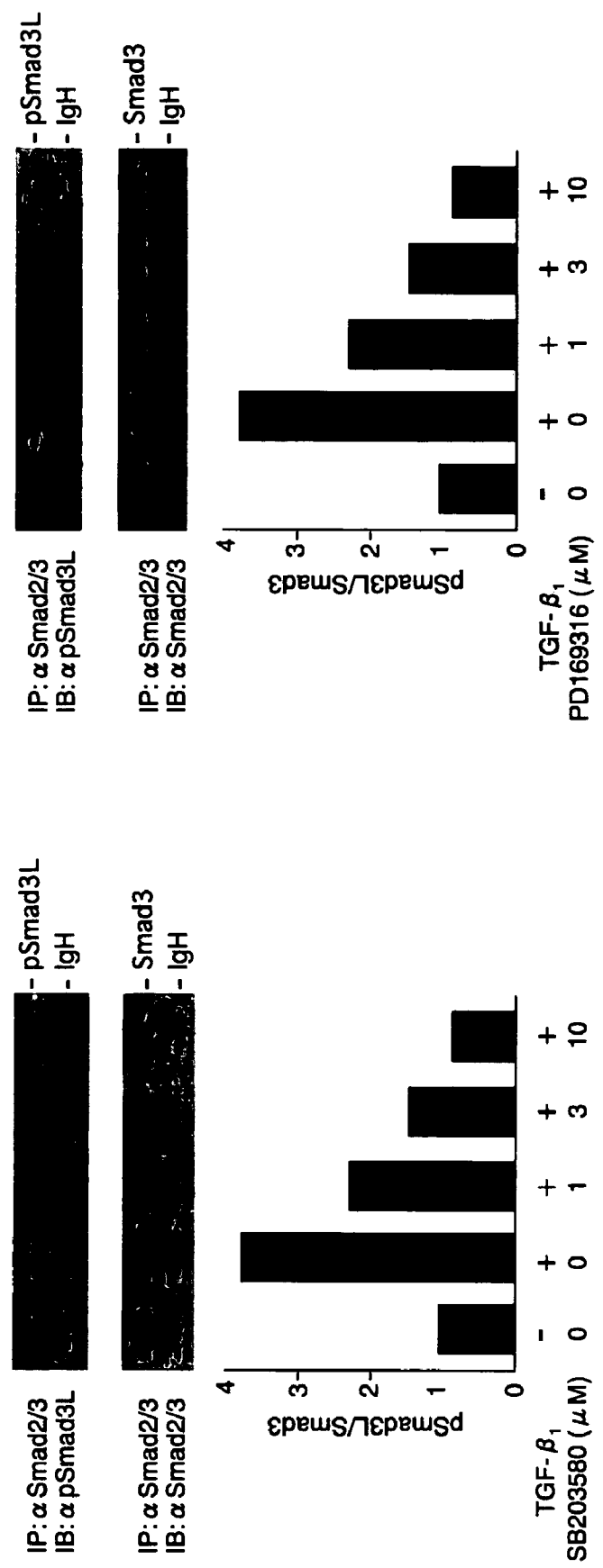
FIG. 3 illustrates an experimental example using a known p38 (kinase) inhibitor.

Example of Detecting Phosphorylation-Inhibiting Compounds in Test System using the Present Antibodies/Experimental Example Using Known p38 (Kinase) Inhibitor (1) Outline of Results Compounds that inhibit phosphorylation of Smad proteins can be screened by treating the compounds with a known p38 inhibitor before treatment with TGF-β. In this test system, p38 (kinase) inhibitors such as SB203580, SB210190 and PD169316 (all from Calbiochem) inhibited phosphorylation in the linker regions of Smad proteins (FIG. 3).

Figure 4:
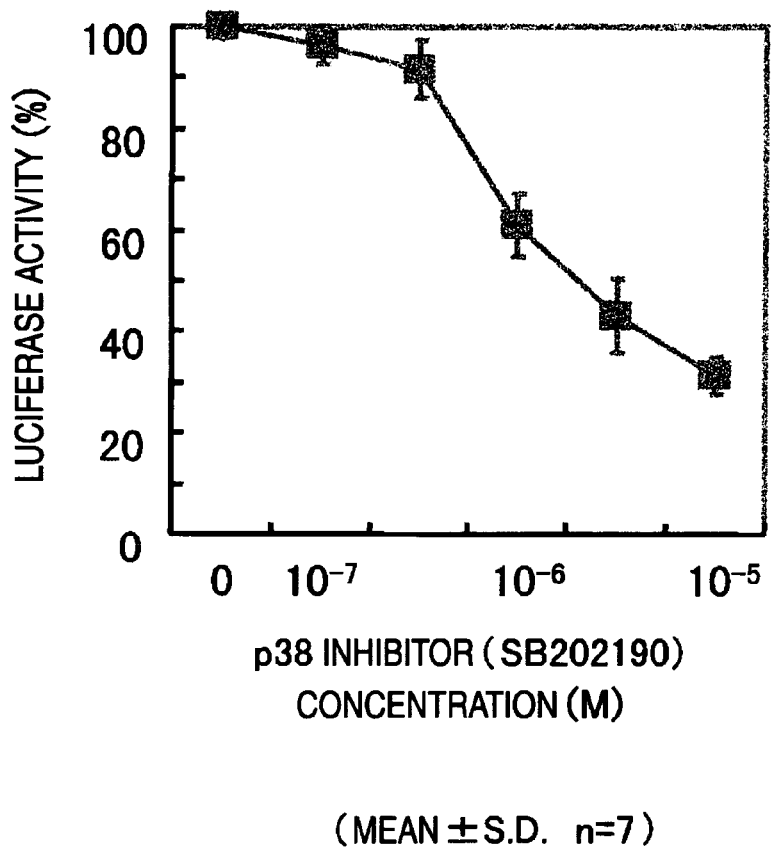
FIG. 4 illustrates the action on the TGF-β-dependent transcription activity of a p38 inhibitor (HepG2 cells)

There has been already reported (F. Furukawa, K. Matsuzaki et. al., Hepatology (2003) 38, 879-889) that in cells in which cDNAs with the phosphorylation sites of their linker regions mutated are expressed, the TGF-β-dependent transcription activity is suppressed. Treatment with p38 inhibitors, which inhibited phosphorylation in the linker regions of Smad proteins, also suppressed the TGF-β-dependent transcription activity (FIG. 4).

As described above, inhibiting Smad3 phosphorylation in the linker region leads to suppressing the activity of Smad3; accordingly, the method of detecting phosphorylation as well as inhibition of phosphorylation using the antibodies enables the screening of compounds that inhibit phosphorylation.

(2) Method

Myofibroblasts (MFB 2×10$^6$ cells/100 mm dish) from rat liver were cultured in DMEM medium (containing 5% fetal bovine serum) for several days and further cultured with 200 pM TGF-β (R&D Systems) for 30 minutes under the serum-free conditions. The cells were homogenized with RIPA buffer (10 mM Tris-HCl, pH 7.8/1% NP40/0.15M NaCl/1 mM EDTA/10 μg/ml aprotinin), and the resultant lysate was centrifuged at 15,000×g. The supernatant was incubated with Smad-specific antibodies and protein G-sepharose (Amersham Bioscience) to obtain immunoprecipitate. After the incubation, part of the precipitate was subjected to SDS-polyacrylamide gel electrophoresis, the obtained gel was transferred onto a PVDF membrane, and immunoblotting was performed using the antibodies specific for phosphorylation of the linker regions and C-terminal regions in Smad2 and Smad3. The detection was carried out by a chemiluminescence technique using HRP-labeled secondary antibody/ anti-IgG, IgH antibody (Amersham Bioscience). The treatment with the compounds was performed 30 minutes before the addition of TGF-β in the same manner as described above. The detected bands were quantified using an imaging analyzer.

The TGF-β-dependent transcriptional activity was determined as previously described. Specifically, pGL3 luciferase expression vector was used in which DNA containing pSmad3-binding sites of the promoter region in plasminogen activator inhibitor I (PAI-I) gene, known as a target gene of TGF-β, was integrated. Into HepG2 cells cultured in RPMI1640 (containing 5% fetal bovine serum) for several days, the luciferase expression vector constructed was introduced by lipofection technique using Superfect (QIAGEN), whereas into MFBFI, the vector was introduced by lipofection technique using lipofectAMINE (invitrogen). Then, 120 minutes after treatment with the compounds, TGF-β was added to the cells, and after 24 to 48 hours, the cells were recovered to determine the luciferase activity as previously described.

Example 3

Figure 5A:
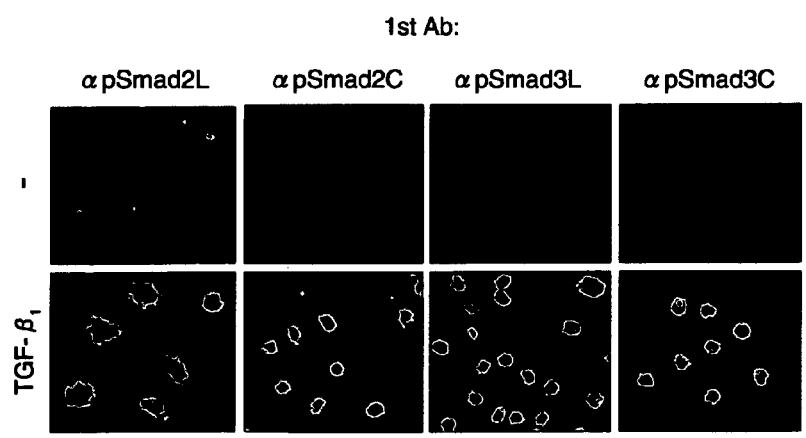
FIG. 5A illustrates the subcellular localization of Smads in cells.
Figure 5B:
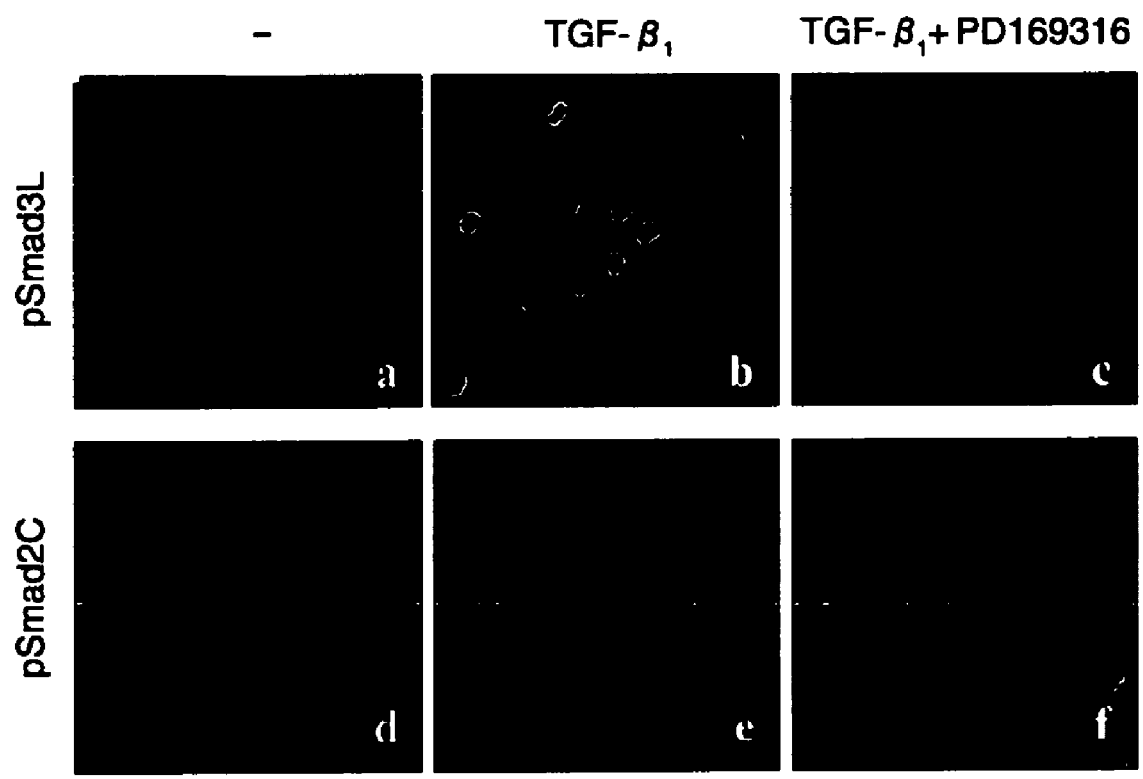
FIG. 5B illustrates the suppression of Smad3 translocation in nuclei by p38 inhibitor.

Detection of Localization of Smad3 Phosphorylated in the Linker Region using Antibody (1) Outline of Results The cells expressing Smad3 were stimulated with TGF-β, and the phophorylation of the linker region was immunohistochemically detected with the specific antibody. The use of the antibody confirmed that Smad3 phosphorylated in the linker region is localized in nuclei. (FIG. 5A). On the other hand, when the cells were treated with p38 inhibitor and then with TGF-β, the phosphorylation of Smad3 in the linker region was inhibited and the accumulation of Smad3 in nuclei was suppressed (FIG. 5B).

Immunohistochemical examination using the antibodies was performed in liver tissue sections from CCl$_4$-treated rat with hepatic fibrosis. By the examination, Smad3 phosphorylated in the linker region was detected specifically in the nuclei of α-SMA positive cells as the disease progress (FIG. 6). This indicates that the use of the antibody enables the confirmation of Smad3 phosphorylated in the linker region in the liver sections during liver disease.

Accordingly, the use of the antibody makes it possible to detect subcellular localization of Smad3 phosphorylated in the linker region, and to evaluate Smad3-mediated signal leading to liver fibrosis.

(2) Method

The detection of subcellular localization was carried out as previously described (Cancer Res.; K. Matsuzaki et al. 60, 1394-1402 (2000)). Specifically, hepatic cells, clone 9 (I. B., Weinstein et al., Cancer Res. 35, 253-263 (1975)), established from rat normal liver were cultured in LAB TEK chambers, incubated with 200 μM TGF-β for 1 hour, and then fixed with 4% paraformaldehyde. The cells were incubated with the primary antibodies (specific antibodies against phosphorylation of the C-terminal regions and the linker regions in Smad2 and Smad3) and anti-FLAG antibody at 4° C. for 16 hours. After washing, the cells were treated with Cy2-labeled goat anti-mouse IgG antibody, and the detection was carried out with a fluorescence microscope.

Sections 4 μm thick were prepared from the frozen specimen of CCl$_4$-treated rat liver, fixed with acetone at 4° C. for 10 minutes, and treated with PBS containing 0.3% hydrogen peroxide at room temperature for 10 minutes. The fixed sections were used to perform immunostaining. The resultant sections were pretreated with normal goat serum, incubated with the primary antibodies (specific antibodies against phosphorylation of the C-terminal regions and the linker regions in Smad2 and Smad3) at 4° C. overnight, and after washing, further incubated with biotinylated goat anti-rabbit IgG (Vector Laboratories) at room temperature for 40 minutes. The detection was performed in such a manner as to incubate the sections with streptavidin-HRP reagent (Vector Laboratories) at room temperature for 30 minutes and the color was developed in PBS containing 0.02% 3,3'-deaminobenzidine tetrahydrochloride and 0.006% hydrogen peroxide.

EXAMPLE 4

(1) Outline of Results

Arbitrary cells were stimulated with TGF-β and recovered after a predetermined time. The homogenate of the recovered cells was immunoprecipitated with the specific antibodies against kinase, the immunoprecipitated sample and a Smad3 recombinant were incubated in vitro to phosphorylate Smad3, and the phosphorylated Smad3 was detected with the specific antibodies. The use of the antibodies confirmed that the linker region of Smad3 was directly phosphorylated by p38 and JNK. Treating this reaction system with candidate drugs makes it possible to screen compounds that inhibit phosphorylation.

(2) Method

Figure 7:
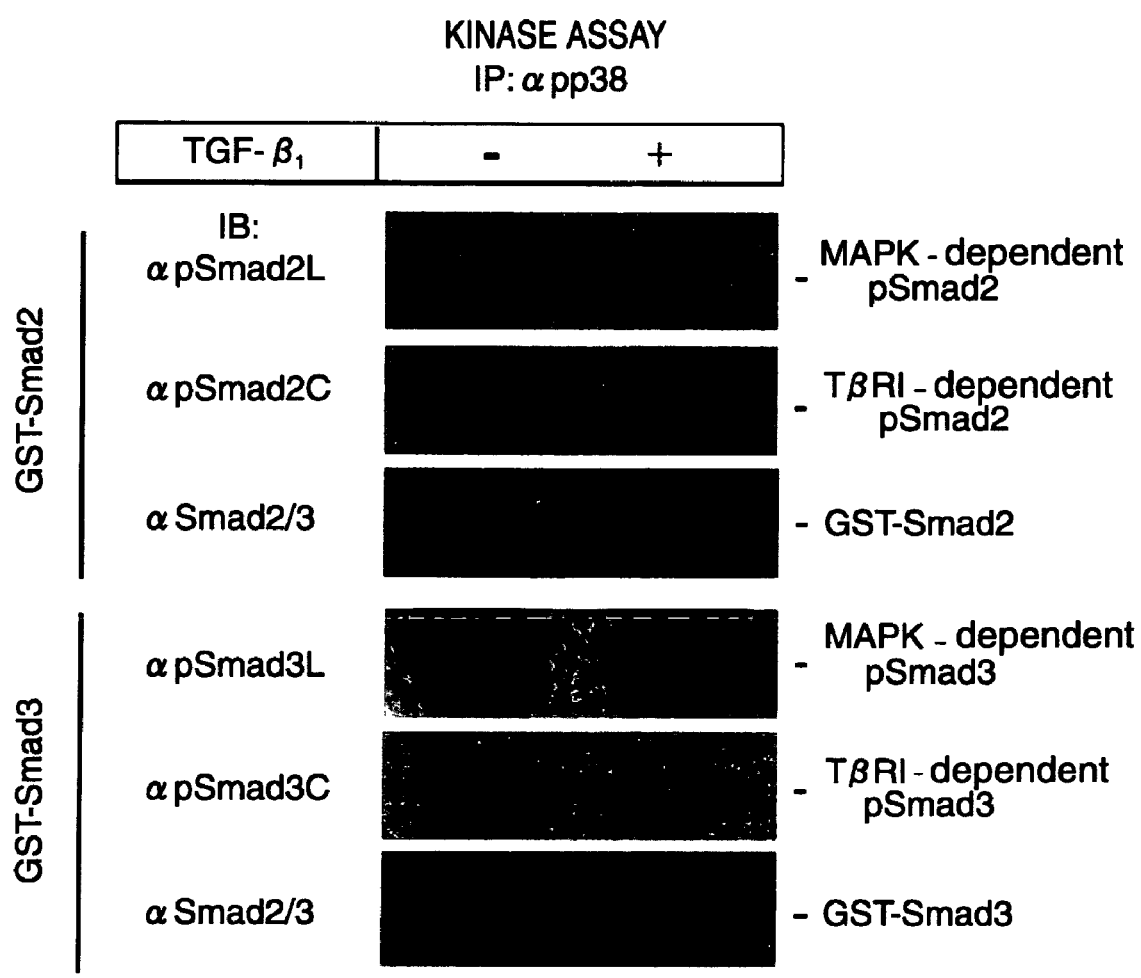
FIG. 7 illustrates the detection of phosphorylated Smads in kinase assay by immunoblotting.

The kinases were prepared in such a manner as to cultivate cells (clone 9) under serum-free conditions for 15 hours, treat the cells with TGF-β, recover the treated cells after 15 to 60 minutes, immunoprecipitate phosphorylated JNK or phosphorylated p38 which are active kinases (these enzymes become active when they are phosphorylated) with their specific antibodies (available from Promega), isolate the phosphorylated JNK or phosphorylated p38 with protein G-Sepharose, and wash and suspend the immunoprecipitated enzymes in a kinase buffer (25 mM Tris-HCl, pH 7.5, 5 mM P-glycerophosphate, 2 mM DTT, 0.1 mM Na$_3$VO$_3$, 10 mM MgCl$_2$). Two micrograms of bacterial recombinant GST-Smad3 and GST-Smad2 were reacted with the enzymes in 50 μl of kinase buffer containing 100 μM ATP. Separation by SDS-polyacrylamide gel electrophoresis was performed, and phosphorylated Smads are detected by immunoblotting technique using the antibodies against phosphorylated Smads. The results are shown in FIG. 7.

EXAMPLE 5

(1) Outline of Results

Phosphorylation dynamics of Smads in human colon cancer tissue was immunohistochemically examined using the antibodies of this invention.

Smad3 phosphorylated in the linker region was detected in the nucleus of the human colon cancer tissue. The phosphorylation of Smad3 in the linker region was increased with the progress of the cancer, indicating its positive correlation with the degree of the malignancy of the cancer. The method of this invention provides not only an index of the activity of oncogenesis stimulating signal, but also useful means for objectively judging the efficacy of drugs for human colon cancer.

(2) Method

Immunohistochemical staining was performed using cells of human advanced colon cancer where no gene mutation was detected in type II TGF-β receptor, Smad2 and Smad4 to examine the phosphorylation dynamics of Smad3 and the subcellular localization of the phosphorylated Smad.

Specifically, a pathological specimen slice of 4 μm in thickness was prepared from a frozen piece of affected region of a patient with colon cancer, fixed in acetone at 4° C. for 10 minutes and treated with PBS containing 0.3% hydrogen peroxide at room temperature for 10 minutes. Immunohistochemical staining was performed with this fixed slice. The slice obtained was pre-treated with normal goat serum, incubated with a primary antibody (antibody specific for the phosphorylation in the linker region of Smad3) at 4° C. for 24 hours, and after washing, further incubated with biotinylated goat anti-rabbit IgG antibody (Vector Laboratories) at room temperature for 40 minutes. Detection was carried out by incubating the slice with streptoavidin-HRP reagent (Vector Laboratories) at room temperature for 30 minutes and developing color with PBS containing 0.02% 3,3'-deaminobenzidine tetrahydrochloride and 0.006% hydrogen peroxide.

For comparison, another immunohistochemical staining was similarly performed by using an antibody (αKi-67) against Ki-67, that is known as a marker for cell proliferation.

(3) Results

The antibody of this invention (apSmad3L) evidently revealed that the linker region of Smad3 was hardly phosphorylated in normal colon crypt, i.e. in a region of tissue including a number of negative cells to the Ki-67 antigen, an index of cell proliferation ability (FIG. 8, apSmad3L, upper part) and that in colon cancer cells, i.e. Ki-67 antigen positive cells, the phosphorylation in the linker region of Smad3 markedly increased (FIG. 8, apSmad3L, lower part). The phosphorylated Smad3 was localized in nuclei of cancer cells. The results are shown in FIG. 8. In this figure, the result of immunohistochemical staining with the antibody against Ki-67 is also shown (aKi-67).

What is claimed is:

1. A polyclonal antibody specific for a phosphorylated linker region in Smad2, obtained from antiserum raised by immunizing a mammal with a phosphorylated product of a peptide including an amino acid sequence in the linker region of Smad2, wherein the phosphorylated product of a peptide including the amino acid sequence in the linker region of Smad2 for the immunization is: Pro Ala Glu Leu p-Ser Pro Thr Thr Leu p-Ser Pro Val Asn His Ser (SEQ ID NO: 1) wherein p-Ser represents phosphorylated serine.

2. A polyclonal antibody specific for a phosphorylated linker region in Smad3, obtained from antiserum raised by immunizing a mammal with a phosphorylated product of a peptide including an amino acid sequence in the linker region of Smad3, wherein the phosphorylated product of a peptide including the amino acid sequence of the linker region of Smad3 for the immunization is: Ala Gly Ser Pro Asn Leu p-Ser Pro Asn Pro Met p-Ser Pro Ala (SEQ ID NO 2) wherein p-Ser represents phosphorylated serine.

3. The polyclonal antibody according to claims 1 or 2, wherein the mammal is a rabbit.

4. The polyclonal antibody according to claims 1 or 2, wherein the raised antiserum is affinity purified with a phosphorylated peptide(s).

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: human
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 1

Pro Ala Glu Leu Ser Pro Thr Thr Leu Ser Pro Val Asn His Ser
1               5                   10                  15

<210> SEQ ID NO 2
<211> LENGTH: 14
<212> TYPE: PRT
<213> ORGANISM: human
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 2

Ala Gly Ser Pro Asn Leu Ser Pro Asn Pro Met Ser Pro Ala
1               5                   10
```

```
<210> SEQ ID NO 3
<211> LENGTH: 9
<212> TYPE: PRT
<213> ORGANISM: human
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 3

Pro Ser Val Arg Cys Ser Ser Met Ser
1               5

<210> SEQ ID NO 4
<211> LENGTH: 9
<212> TYPE: PRT
<213> ORGANISM: human
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 4

Pro Ser Ile Arg Cys Ser Ser Val Ser
1               5
```